United States Patent [19]

Suetsugu et al.

[11] Patent Number: 5,306,713
[45] Date of Patent: Apr. 26, 1994

[54] HIGHLY ACTIVE ANTIOXIDANT OF TOCOPHERYL ASCORBYL PHOSPHATE

[75] Inventors: Keiko Suetsugu, Yokohama; Kazumi Ogata, Toyonaka; Kenichi Yoshida, Itami; Keiichi Uehara; Kenichi Tomita, both of Yokohama, all of Japan

[73] Assignees: Shiseido Company Ltd., Tokyo; Senju Pharmaceutical Co, Ltd., Osaka, both of Japan

[21] Appl. No.: 741,988

[22] Filed: Aug. 7, 1991

Related U.S. Application Data

[63] Continuation of Ser. No. 364,051, Jun. 8, 1989, abandoned.

[51] Int. Cl.$^5$ .................. A61K 31/66; A61K 31/355; A61K 31/34
[52] U.S. Cl. .................. 514/100; 514/120; 514/129; 514/141; 514/458; 514/474; 426/545; 426/547
[58] Field of Search ............... 514/474, 458, 100, 120, 514/

[56] References Cited

U.S. PATENT DOCUMENTS

| | | | |
|---|---|---|---|
| 3,637,772 | 1/1972 | Klaui et al. | 260/398.5 |
| 3,752,832 | 8/1973 | Maruyama et al. | 260/398.5 |
| 3,903,317 | 9/1975 | Cort | 426/545 |
| 3,959,321 | 5/1976 | McKenna | 260/398.5 |
| 4,564,686 | 1/1986 | Ogata | 549/220 |
| 4,765,927 | 8/1988 | Nomura et al. | 252/400.2 |
| 4,888,329 | 12/1989 | Ogata et al. | 514/100 |

OTHER PUBLICATIONS

CA: vol. 111(6):45280t (1989).

Primary Examiner—Frederick E. Waddell
Assistant Examiner—T. J. Criares
Attorney, Agent, or Firm—Sprung Horn Kramer & Woods

[57] ABSTRACT

A highly active antioxidant composed of a diester of phosphoric acid with tocopherol and ascorbic acid or a salt thereof used to stabilize other materials.

2 Claims, No Drawings

HIGHLY ACTIVE ANTIOXIDANT OF TOCOPHERYL ASCORBYL PHOSPHATE

This application is a continuation of application Ser. No. 364,051, filed Jun. 8, 1989 now abandoned.

BACKGROUND OF THE INVENTION

1. Field of the Invention

The present invention relates to a novel and safe antioxidant. More specifically, it relates to an antioxidant, for cosmetics, medicines and foods, which is composed of, as an effective ingredient, a diester of phosphoric acid with tocopherol and ascorbic acid and/or a salt thereof.

2. Description of the Related Art

In cosmetics, medicines, and foods comprising a base material which is easily deteriorated by oxidation, such oxidation is increased by contact with air and the quality is drastically degraded. Accordingly, an antioxidant is used to prevent this deterioration by oxidation.

As the antioxidant heretofore used, there can be mentioned synthetic antioxidants such as butylhydroxytoluene (BHT) and butylhydroxyanisole (BHA), and natural antioxidants such as D-α-tocopherol.

Synthetic antioxidants such as BHT and BHA have a relatively excellent anti-oxidizing effect, but since doubts have arisen with regard to the safety thereof, the use of these synthetic antioxidants is now being reconsidered.

A natural antioxidant, especially tocopherol, is highly evaluated with respect to safety but is defective in that the effect is not extensive. Moreover, the natural antioxidant has problems with regard to the supply source and the solubility. Therefore, an antioxidant able to exert a satisfactory anti-oxidizing effect when applied to an aqueous product is not known.

SUMMARY OF THE INVENTION

Accordingly, the objects of the present invention are to eliminate the above-mentioned disadvantages of the prior art and to provide an antioxidant capable of safely and effectively preventing the deterioration of a material by oxidation.

Other objects and advantages of the present invention will be apparent from the following description.

In accordance with the present invention, there is provided an antioxidant comprising a diester of phosphoric acid with tocopherol and ascorbic acid or a salt thereof (hereinafter referred to as phosphoric acid diester).

DESCRIPTION OF THE PREFERRED EMBODIMENTS

The phosphoric acid diester according to the present invention has a structure in which, of three hydroxyl groups of phosphoric acid, two hydroxyl groups are esterified by one hydroxyl group each of tocopherol and ascorbic acid, and the phosphoric acid diester is preferably represented by the following formula [1]:

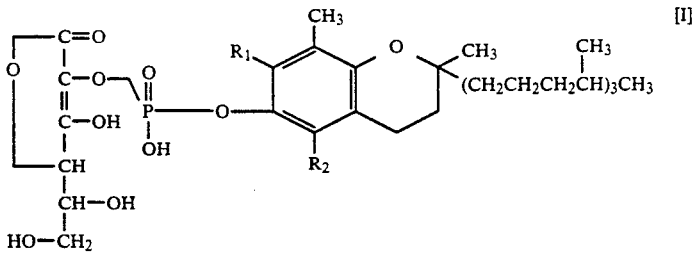

In the formula [1], $R_1$ and $R_2$ independently represent a member shown below according to $\alpha$-, $\beta$-, $\gamma$- or $\delta$-tocopherol.

|   | $R_1$ | $R_2$ |
|---|-------|-------|
| α | CH₃ | CH₃ |
| β | H | CH₃ |
| γ | CH₃ | H |
| δ | H | H |

The phosphoric acid diester according to the present invention can be prepared, for example, according to the following process. Tocopherol is reacted with a halogenophosphorylating agent; this reaction readily advances in a non-reactive solvent in the presence of a deacidifying agent; the resultant product is reacted with ascorbic acid having the hydroxyl groups in the 5- and 6-positions protected by protecting groups; this reaction advances in a solvent such as tetrahydrofuran in the presence of a deacidifying agent; and then the protecting groups are eliminated.

The phosphoric acid diester is obtained by the above-mentioned procedures.

The phosphoric acid diester of the present invention can be used in the form of either a free acid or a salt. As the salt, there can be mentioned an organic amine salt and an inorganic salt. As the organic amine salt, there can be mentioned an aminomethylpropanol salt, an aminohydroxylmethylpropane-diol salt, an aminomethylpropane diol salt, an isopropanolamine salt, a monoethanolamine salt, a diethanolamine salt, a triethanolamine salt, a morpholine salt, a glucosamine salt, and a diisopropanolamine salt. As the inorganic salt, there can be mentioned a sodium salt, a potassium salt, a lithium salt, a calcium salt, and a magnesium salt. Of these salts, for example, the sodium salt and potassium salt are soluble in water but the calcium salt, for example, is insoluble in water. Therefore, an appropriate salt can be selected according to the intended object. To convert the free acid to an alkali salt, preferably the free acid is neutralized in an alkaline substance.

The phosphoric acid diester and its salt can be freely dissolved in water, although tocopherol is not soluble in water.

The phosphoric acid diester of the present invention or its salt is incorporated in an amount of 0.001% to 5% by weight, preferably 0.005% to 0.2% by weight, based on a cosmetic, medicine or food or a starting material thereof.

The antioxidant of the present invention has an outstanding effect on bases, for example, oils having an unsaturated bond, glycerol and glycerol derivatives such as polyglycerol, polyglycerol fatty acid esters and polyglycerol alkyl ethers, and substances having an oxyalkylene chain, such as polyethylene glycol, polyethylene glycol fatty acid esters, polyoxyethylene alkyl ethers and polyoxyethylene polyoxypropylene alkyl ethers, and various cosmetics, medicines and foods formed by incorporating these bases into either aqueous systems or oil systems. Especially, the antioxidant of the present invention has a surprising effect on polar substances and aqueous products. Moreover, it is expected that a further enhanced effect will be obtained if the antioxidant of the present invention is used in combination with another antioxidant such as tocopherol or an organic acid, or BHT or BHA.

The antioxidant of the present invention has the following advantages.

(1) Reduction of the pH value of product can be controlled;

(2) Formation of formalin and the like can be controlled;

(3) Worsening of a smell of a product can be controlled.

(Examples)

The present invention will now be described in detail with reference to, but is by no means limited to, the following preparation examples and experimental examples.

Preparation Example 1

Preparation of potassium L-ascorbic DL-α-tocopherol phosphate

In 50 ml of benzene was dissolved 6.12 g of phosphorus oxytrichloride, and a mixed solution of 8.6 g (0.02 mole) of DL-α-tocopherol and 9.5 g of pyridine in 50 ml of benzene was added dropwise to the above solution while stirring. After termination of the dropwise addition, the mixture was further stirred for 3 hours. The precipitated pyridine hydrochloride was removed by filtration, the filtrate was concentrated under a reduced pressure, and 30 ml of benzene was added to the residual oil.

Separately, 5.2 g (0.024 mole) of 5,6-isopropylidene-ascorbic acid obtained by acetonation of L-ascorbic acid and 3.2 g of pyridine were dissolved in 120 ml of tetrahydrofuran, the above benzene solution was added dropwise to the tetrahydrofuran solution while stirring, and after termination of the dropwise addition, stirring was conducted for about another 1 hour. The precipitated pyridine hydrochloride was removed by filtration, and the solvent was removed from the filtrate by distillation under a reduced pressure. The obtained oil was dissolved in 30 ml of ethyl alcohol, 150 ml of 1N hydrochloric acid was added to the solution, the mixture was heated and refluxed for about 20 minutes, cooled, extracted with ethyl acetate, and dried with anhydrous sodium sulfate. Ethyl acetate was then removed by distillation, and a crude free acid was obtained as the residue.

This crude free acid was dissolved in about 100 ml of ethyl alcohol, and a solution of potassium hydroxide in ethyl alcohol was gradually dropped into the above solution until the pH value of the solution became neutral, whereby a slightly brownish white crystal was precipitated. The crystal was recovered by filtration and recrystallized from water-ethyl alcohol-acetone to obtain 7.5 g of a white powdery crystal.

Melting point: Carbonization gradually began at about 210° C.

Ultraviolet absorption spectrum (UV): A maximum absorption appeared at about 257 nm.

Silica gel thin layer chromatography: Rf=0.81 (ethyl alcohol/acetone/water=10/4/1) Elementary analysis values as $C_{35}H_{55}C_1.PK_2.H_2O$:
Calculated: C=55.09%, H=7.53%
Found: C=55.32%, H=7.65%

Preparation Example 2

Preparation of sodium L-ascorbic DL-α-tocopherol phoschate

In 30 ml of water was dissolved, 5 g of potassium L-ascorbic DL-α-tocopherol phosphate obtained in Preparation Example 1, the solution was made acidic by an addition of hydrochloric acid, and extracted with ethyl acetate. Ethyl acetate was removed from the extract by distillation to obtain L-ascorbic DL-α-tocopherol phosphate in the form of a free acid (UV absorption spectrum appeared at 285 nm in water). The free acid was dissolved in ethyl alcohol, and a 30% solution of sodium hydroxide was gradually added to the solution until the solution became neutral, whereby a white crystal was obtained. The white crystal was recovered by filtration, washed with ethyl alcohol, and dried to obtain about 4 g of the intended salt.

Elementary analysis values as $C_{35}H_{55}O_1.PNa_2.H_2O$:
Calculated: C=57.52%, H=7.86%
Found: C=57.65%, H=7.98%

Experimental Example 1

As the example of the present invention, 2 mg of the sodium salt of phosphoric acid diester obtained in Preparation Example 2 was dissolved in 10 g of a 50% aqueous solution of triethylene glycol (supplied by Nakarai Chemicals Co., Ltd.), the solution was stored in a thermostat tank maintained at 50° C. for 3 or 6 days, and the amount of formalin was measured by colorimetry.

Triethylene glycol free of any antioxidant as Comparison Example 1, triethylene glycol in which ascorbic acid was added in the same amount as in the Example of the present invention, as Comparison Example 2, and triethylene glycol in which mixed tocopherol was incorporated in the same amount as in the example of the present invention, as Comparison Example 3, were tested in the same manner as described above.

The results are shown in Table 1.

TABLE 1

| | | Just After Preparation | After 3 Days | After 6 Days |
|---|---|---|---|---|
| Comparison Example 1 | — | 0.1 | 4.7 | 65.8 |
| Comparison Example 2 | ascorbic acid | 0.1 | 39.6 | 111.7 |
| Comparison Example 3 | mixed tocopherol | 0.1 | 19.7 | 87.3 |
| Example of present invention | sodium salt of phosphoric acid diester | 0.1 | 1.7 | 15.5 |

As apparent from the results shown in Table 1, the sodium salt of phosphoric acid diester has a much higher anti-oxidizing effect than that obtained by the use of ascorbic acid or tocopherol alone.

Experimental Example 2

The sample of the Example of the present invention and Comparison Examples 1, 2, and 3 in Experimental Example 1, obtained after 6 days storage, were evaluated with respect to the smell thereof.

The evaluation was made by three experts.

The results are shown in Table 2.

TABLE 2

|  | Antioxidant | Judgement of Smell |
|---|---|---|
| Comparison Example 1 | None | − |
| Comparison Example 2 | Ascorbic | − |
| Comparison Example 3 | Mixed tocopherol | − |
| Example of present invention | Sodium salt of phosphoric acid diester | + |

Note
+: no smell of rancidity
−: strong smell of rancidity

Experimental Example 3

The anti-oxidizing effect of the sodium salt of phosphoric acid diester prepared in Preparation Example 2 against the oxidation of a phospholipid (egg lecitin)/ethanol mixed micell by $Fe^{2+}$·ascorbic acid was examined.

About 78 mg of egg lecitin was dissolved in 2 ml of ethanol, and 5 mM HEPES buffer solution (pH 7.2) was gradually added to the solution with ice cooling under the application of an ultrasonic wave (50 W) to form a suspension, until the total amount was 100 ml. Then, 200 µl of a $2.6 \times 10^{-4}$ M aqueous solution of the sodium salt of phosphoric acid diester was added to 1000 µl of the so-formed liquid. Then 50 µl of a $5.0 \times 10^{-5}$ M aqueous solution of sodium ascorbate and 50 µl of a $2.5 \times 10^{-6}$ M aqueous solution of ferrous sulfate were added to the mixture, and oxidation was carried out for 15 minutes in a water bath at 25° C. After the reaction, 50 µl of a 0.1% solution of hydroquinone in ethanol was immediately added to stop the reaction. Then 200 µl of 20% (W/V) trichloroacetic acid, 0.35% thiobarbituric acid (supplied by Merck) and 2000 µl of a 50% (V/V) aqueous solution of acetic acid were added to the mixture, and the resulting liquid was heated at 100° C. for 15 minutes under reflux cooling. After cooling, the absorbance at 450 to 600 nm was measured by a spectrophotometer. The increase of the absorption in the vicinity of about 530 to about 540 nm in the obtained curve was measured. The inhibition ratio was determined by comparing the obtained result with the result obtained at the blank test not using the test liquid.

The results are shown in Table 3.

TABLE 3

| Antioxidant | Inhibition Ratio |
|---|---|
| sodium salt of phosphoric acid diester ($4.0 \times 10^{-5}$ M) | 99.1% |

As seen from Table 3, the sodium salt of phosphoric acid diester substantially completely inhibited the oxidation.

Formulation examples of cosmetics, foods and medicines comprising the antioxidant of the present invention will now be described. Note, the scope of the present invention is not limited by these examples.

| Formulation Example 1 (Milky Lotion) | wt % |
|---|---|
| Stearic acid | 2.5 |
| Cetyl alcohol | 1.5 |
| Vaseline | 5.0 |
| Liquid paraffin | 10.0 |
| Polyoxyethylene (10 moles) mono-oleate | 2.0 |
| Polyethylene glycol 1500 | 3.0 |
| Triethanolamine | 1.0 |
| Ascorbic acid | 5.0 |
| Na salt of phosphoric acid diester | 0.1 |
| Purified water | balance |
| Perfume | q.s. |
| Antiseptic agent | q.s. |

(Preparation Process)

Polyethylene glycol 1500, triethanolamine, ascorbic acid, and the Na salt of phosphoric acid diester were added to purified water, the mixture was heated to form a solution, and the solution was maintained at 70° C. (aqueous phase). Other components were mixed, heated and melted, and the melt was maintained at 70° C. (oil phase). The oil phase was added to the aqueous phase, a preliminary emulsification was carried out, and the mixture was homogeneously emulsified by a homomixer. After the emulsification, the formed emulsion was cooled to 30° C. while stirring.

| Formulation Example 2 (Health Drink) | wt % |
|---|---|
| Fructose-glucose liquid | 17.9 |
| Honey | 0.1 |
| Citric acid | 82 mg % |
| DL-Malic acid | 41 mg % |
| L-Aspartic acid | 20 mg % |
| L-Arginine | 20 mg % |
| Nicotinic acid amide | 10 mg % |
| Sodium glutamate | 1 mg % |
| Thiamin NDS | 0.17 mg % |
| Riboflavin | 0.25 mg % |
| Pyridoxine hydrochloride | 0.5 mg % |
| L-Ascorbic acid | 50 mg % |
| Na salt of phosphoric acid diester | 0.1% |
| Purified water | balance |
| Perfume | q.s. |

| Formulation Example 3 (Ointment) | wt % |
|---|---|
| γ-Oryzanol | 1.0 |
| Na salt of phosphoric acid diester | 0.1 |
| Hydrophilic ointment base | balance |

(Preparation Process)

The γ-Oryzanol and the Na salt of the phosphoric acid diester were mixed with a small amount of the hydrophilic ointment base, the remainder of the hydrophilic ointment base was gradually added to the mixture to the total amount (100%), and a homogeneous composition was prepared.

The recipe of the hydrophilic ointment base used was as follows.

| -Hydrophilic Ointment Base- | wt % |
|---|---|
| Cetanol | 6.0 |
| Polyoxyethylene (30 moles) cetyl ether | 2.0 |
| Glyceryl monostearate (self-emulsifiable type) | 10.0 |
| Liquid paraffin | 10.0 |
| White vaseline | 5.0 |
| Methylparaben | 0.1 |
| Butylparaben | 0.1 |
| Propylene glycol | 10.0 |

We claim:

1. A method of preventing oxidation deterioration of a material susceptible to oxidative deterioration which comprises mixing said material with an antioxidant-effective amount of a diester of phosphoric acid with tocopherol and ascorbic acid of the formula

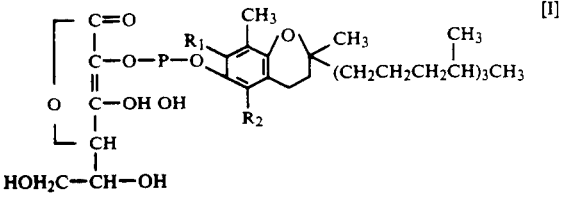

wherein $R_1$ represents H or $CH_3$ and $R_2$ represents H or $CH_3$, or a salt thereof.

2. A method as claimed in claim 1, wherein the amount of the diester of phosphoric acid or its salt is in an amount of 0.001% to 5% by weight based on the weight of the material.